United States Patent
Simpson et al.

(10) Patent No.: US 9,517,241 B2
(45) Date of Patent: Dec. 13, 2016

(54) AMELIORATION OF INTESTINAL FIBROSIS AND TREATMENT OF CROHN'S DISEASE

(71) Applicant: THE REGENTS OF THE UNIVERSITY OF MICHIGAN, Ann Arbor, MI (US)

(72) Inventors: Robert U. Simpson, Ann Arbor, MI (US); Peter D. R. Higgins, Ann Arbor, MI (US); Laura A. Johnson, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 0 days.

(21) Appl. No.: 15/051,850

(22) Filed: Feb. 24, 2016

(65) Prior Publication Data

US 2016/0166587 A1   Jun. 16, 2016

Related U.S. Application Data

(62) Division of application No. 14/134,587, filed on Dec. 19, 2013, now Pat. No. 9,370,527.

(60) Provisional application No. 61/746,969, filed on Dec. 28, 2013.

(51) Int. Cl.
| | | |
|---|---|---|
| A61K 31/59 | (2006.01) | |
| C07C 401/00 | (2006.01) | |
| A61K 9/00 | (2006.01) | |
| A61K 31/592 | (2006.01) | |
| A61K 45/06 | (2006.01) | |

(52) U.S. Cl.
CPC ............ *A61K 31/59* (2013.01); *A61K 9/0053* (2013.01); *A61K 31/592* (2013.01); *A61K 45/06* (2013.01)

(58) Field of Classification Search
USPC ....................................... 514/167
See application file for complete search history.

(56) References Cited

U.S. PATENT DOCUMENTS

2005/0070513 A1   3/2005   Cantorna

FOREIGN PATENT DOCUMENTS

| WO | 03/106629 A2 | 12/2003 |
|---|---|---|
| WO | 2005/027839 A2 | 3/2005 |
| WO | 2005/039592 A1 | 5/2005 |
| WO | 2005/051936 A1 | 6/2005 |
| WO | 2006/036813 A2 | 4/2006 |

OTHER PUBLICATIONS

Daniel, Carolin et al. (2006) The New Low Calcemic Vitamin D Analog 22-Ene-25-Oxa-Vitamin D Prominently Ameliorates T Helper Cell Type 1-Mediated Colitis in Mice. The Journal of Pharmacology and Experimental Therapeutics. vol. 319(2); pp. 622-631.

Miheller, Pal et al. (2009). Comparison of the Effects of 1,25 Dihydroxyvitamin D and 25 Hydroxyvitamin D on Bone Pathology and Disease Activity in Crohn's Disease Patients. Inflammatory Bowel Diseases. vol. 15(11). pp. 1656-1662.

Wang, Tian-Tian et al. (2010). Direct and Indirect Induction by 1,25-Dihydroxyvitamin D3 of the NOD2/CARD15-Defensin ?2 Innate Immune Pathway Defective in Crohn Disease. The Journal of biological Chemistry. vol. 285(4). pp. 2227-2231.

Laverny, Gilles et al. (2010). Efficacy of a potent and safe vitamin D receptor agonist for the treatment of inflammatory bowel disease. Immunology Letters. vol. 131(1). pp. 49-58.

Martinesi, Maria et al. (2010). Down-regulation of adhesion molecules and matrix metalloproteinases by ZK 156979 in inflammatory bowel diseases. Clinical Immunology. vol. 136(1). pp. 51-60.

Stio, Maria et al. (2004) Effect of anti-TNF therapy and vitamin D derivatives on the prliferation of peripheral blood mononuclear cells of Crohn's disease. Digestive Diseases & Sciences. vol. 49(2):328-335.

Stio, Maria et al. (2006) Interaction among vitamin D-3 analogue KH 1060, TNF-a, and vitamin D receptor protein in peripheral blood mononuclear cells of inflammatory bowel disease patients. International Immunopharmacology. vol. 6(7):1083-92.

Stio, Maria et al. (2007) The Vitamin D analogue TX 527 blocks NF-kB activation in peripheral blood mononuclear cells of patients with Crohn's disease. The Journal of Steroid Biochemistry and Molecular Biology. 103(1):51-60.

V. Vegesna et al. (2003). Ability of potent vitamin D3 analogs to inhibit growth of prostate cancer cells in vivo. Anticancer Research. vol. 23(1A), pp. 283-289.

*Primary Examiner* — Kathrien Cruz

(74) *Attorney, Agent, or Firm* — Harness, Dickey & Pierce, PLC

(57) ABSTRACT

Methods of treating patients with inflammatory bowel disease, intestinal fibrosis, or Crohn's disease involve administering a therapeutic amount of CARD-024 or related compound.

18 Claims, 5 Drawing Sheets

AMELIORATION OF INTESTINAL FIBROSIS AND TREATMENT OF CROHN'S DISEASE

CROSS REFERENCE TO EARLIER APPLICATIONS

This application is a divisional of U.S. patent application Ser. No. 14/134,587 filed on Dec. 19, 2013, which claims the benefit of U.S. Provisional Application No. 61/746,969 filed on Dec. 28, 2013. The entire disclosures of each of the above applications are incorporated herein by reference.

GOVERNMENT SUPPORT

This invention was made with government support under DK080172 and HL074894 awarded by the National Institutes of Health. The Government has certain rights in the invention.

INTRODUCTION

Crohn's disease (CD) is a chronic, progressive intestinal disorder characterized by cycles of intestinal inflammation and mucosal healing. Despite the advent of powerful anti-inflammatory therapies, 70% of patients ultimately develop fibrostenotic disease for which there are no effective pharmacologic therapies (Andres and Friedman, 1999; Cosnes et al., 2002; Loftus, 2004). Patients with CD have an increased prevalence of vitamin D deficiency, but it is not clear whether vitamin D deficiency is a contributing factor to fibrosis, or merely a disease consequence (Harries et al., 1985; Siffledeen et al., 2003). In other organ systems, including kidney, liver, lung, skin and heart, vitamin D deficiency is associated with fibrosis (Li et al., 2005; Rahman et al., 2007; Ramirez et al., 2010; Tan et al., 2006; Weishaar et al., 1990; Zhang et al., 2011).

Vitamin D analogs have been shown to reduce fibrosis in cell culture and animal models of cardiac, kidney, and renal fibrosis (Li et al., 2005; Mancuso et al., 2008; Tan et al., 2006; Zhang et al., 2010). In CD, activated subepithelial myofibroblasts are the major contributor to intestinal fibrosis (Powell et al., 1999; Tomasek et al., 2002). In colonic myofibroblasts, TGFβ induces differentiation and a pro-fibrotic phenotype, characterized by stress fiber formation (Brenmoehl et al., 2009; Simmons et al., 2002) and induction of "-smooth muscle actin protein expression. In other myofibroblast lineages, including lung, heart, and kidney, extracellular matrix (ECM) stiffness alone stimulates a pro-fibrotic phenotype (Arora et al., 1999; Liu et al., 2010; Olsen et al., 2011), however the effect of matrix stiffness upon colonic myofibroblasts is unknown.

Though calcitriol (vitamin D) and vitamin D analogs have been clinically used for several diseases, including hyperparathyroidism, toxic hypercalcemic effects have been reported, underscoring the need for a vitamin D analog with minimal hypercalcemic effects.

SUMMARY

CARD-024 attenuated the pro-fibrotic response of colonic myofibroblasts to high matrix stiffness, suggesting that CARD-024 and analogous compounds can ameliorate intestinal fibrosis. Hence, a therapy for treating intestinal fibrosis, inflammatory bowel disease, or Crohn's disease involves administering to a subject diagnosed with the condition or disease a composition containing a therapeutically effective amount of a compound of Formula (I)

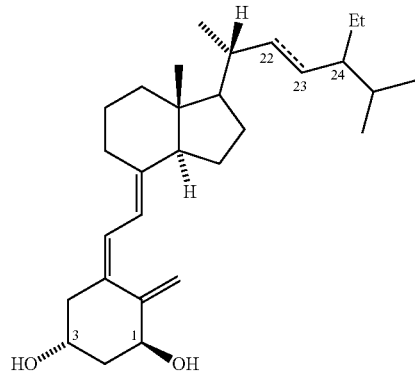

wherein Et is ethyl, wherein the dashed line indicates a single bond or a double bond in the E configuration between carbon 22 and carbon 23, and wherein the configuration at carbon 24 to which Et is attached is in the R configuration or the S configuration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION

Figure 1:
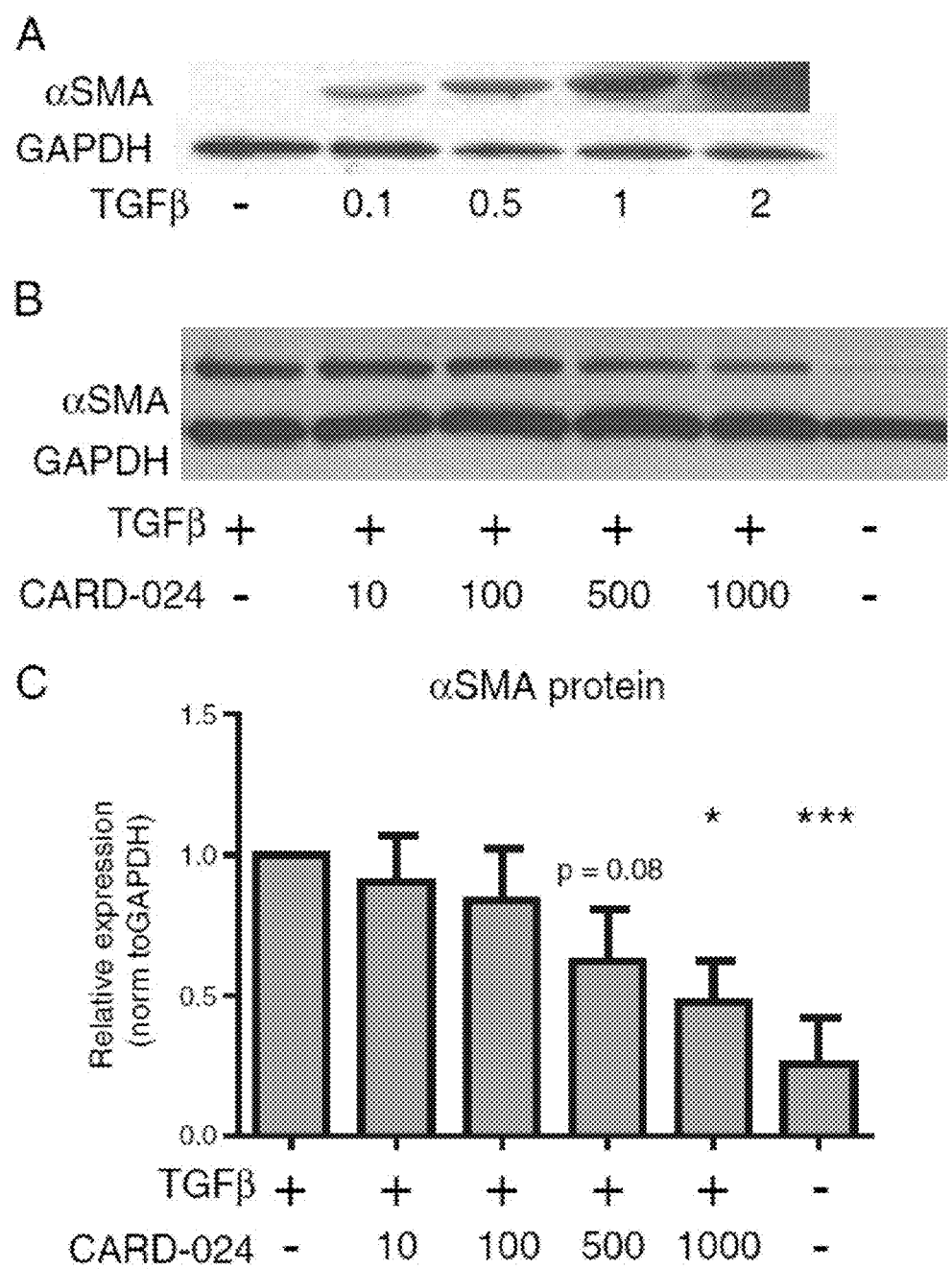
FIG. 1—Effect of CARD-024 on TGFβ stimulated colonic myofibroblasts. (A) Representative Western blot of αSMA protein expression in Ccd-18co cells stimulated with increasing doses of TGFβ (0.1-2 ng/ml). (B) Representative Western blot illustrating αSMA protein expression in response to treatment with TGFβ and increasing amounts of CARD-024 (10-1000 nM) compared to TGFβ treated or untreated cells. In (A) and (B) GAPDH expression is used as a protein loading control. (C) Quantification of αSMA protein expression as normalized to GAPDH in Ccd-18co cells treated with TGFβ and 10-1000 nM CARD-024. Results are from three independent experiments. (*pb0.05, ***pb0.001).

The following abbreviations are used: CD is Crohn's disease; ECM is extracellular matrix; TGFβ is transforming growth factor beta; and αSMA is alpha-smooth muscle actin. Formula (I) and Formula (II) are annotated with IUPAC numbering on some of the carbon atoms for clarity and easy reference. "Mcg" or "mcg" is used as an abbreviation for micrograms.

In one embodiment, a method of treating a subject to relieve the symptoms of inflammatory bowel disease involves administering to the subject a therapeutically effective dose of a compound of Formula (I)

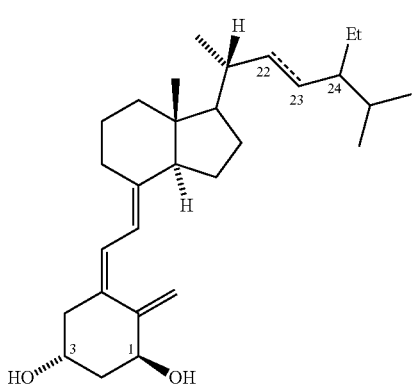

(I)

In Formula (I), wherein Et is ethyl, the dashed line indicates a single bond or a double bond in the E configuration between carbon 22 and carbon 23, and the configuration at carbon 24, to which Et is attached, is in the R configuration or the S configuration. Mixtures of compounds of Formula (I) can also be administered. In a particular embodiment, the compound of Formula (I) includes CARD-024.

In various embodiments, the method includes administering to the subject a composition containing a compound of Formula (I) and a pharmaceutically acceptable carrier. Advantageously, the composition is formulated as a tablet or a capsule, in non-limiting examples. In these and other embodiments, the method can be used to treat a subject diagnosed with or otherwise exhibiting the symptoms of Crohn's disease.

In another embodiment, a method of ameliorating intestinal fibrosis in a subject involves administering to the subject a composition comprising a compound of Formula (I). In a particular embodiment, the compound of Formula (I) has a single bond between carbon 22 and carbon 23, wherein in addition the carbon at position 24 is in S configuration, the R configuration, or a mixture of R and S. In another particular embodiment, the compound of Formula (I) has a double bond in the E configuration between carbon 22 and carbon 23, again with the asymmetric carbon 24 being in the R configuration, the S configuration, or in a combination of R and S. In non-limiting examples, the subject to whom treatment is administered is diagnosed with inflammatory bowel disease or with Crohn's disease. In various embodiments, the subject is a human subject.

In yet another embodiment, method for treating a subject diagnosed with Crohn's disease includes administering to the subject a composition comprising a therapeutically effective amount of a composition containing a compound according to Formula (I) or Formula (II) and a pharmaceutically acceptable carrier

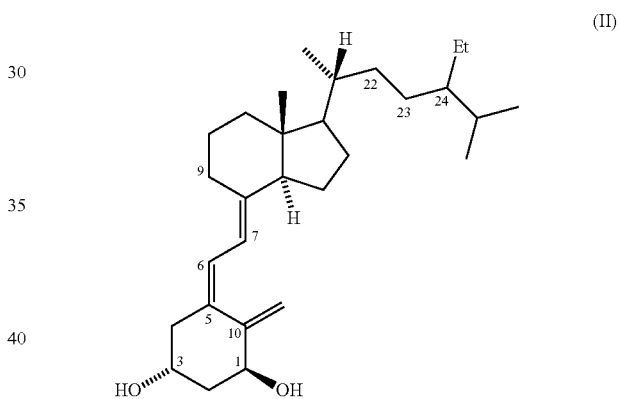

(II)

In a particular embodiment, the composition comprises CARD-024. In other embodiments, the asymmetric carbon 24 is in the R,S configuration, in the R configuration, or is in the S configuration. In various embodiments, suitable doses to be administered in the methods herein range from 5 mcg to 500 mcg of the compound. In embodiments, 1 to 4 doses per day of the composition are administered to the subject. In an exemplary embodiment, the subject is treated by administering the compound of Formula (I) in a delayed release composition containing 20 to 1000 mcg of the compound, for example once a day.

Compounds of Formula (I) have been found to be effective in a model system, where they attenuate the pro-fibrotic response to TGFβ or substrate stiffness in colonic myofibroblasts. As such they are candidates for treating certain symptoms related to diseases, conditions, or syndrome involving a pro-fibrotic response.

Intestinal fibrosis is one of the major complications of Crohn's disease (CD) for which there are no effective pharmacological therapies. Vitamin D deficiency is common in CD, though it is not known whether this is a contributing factor to fibrosis, or simply a consequence of the disease itself. In CD, fibrosis is mediated mainly by activated intestinal myofibroblasts during remodelling of extracellular matrix in response to wound healing.

In the present teachings, we investigated the effects of CARD-024, a compound with minimal hypercalcemic effects, on the pro-fibrotic response of intestinal myofibroblasts to two fibrogenic stimuli: TGFβ stimulation and culture on a physiologically stiff matrix comparable to a Crohn's disease stricture. TGFβ1 stimulated a fibrogenic phenotype in Ccd-18co colonic myofibroblasts, characterized by an increase in actin stress fibers and mature focal adhesions, increased αSMA protein expression, and induction of fibrogenic genes including col1A1, Fn1, MLCK, and ET-1. CARD-024 repressed αSMA protein expression in a dose-dependent manner but had minimal impact on fibrogenic gene expression.

Culture of colonic myofibroblasts on physiological high stiffness substrates induced morphological changes with increased actin stress fibers and focal adhesion staining, induction of αSMA protein expression, FAK phosphorylation, induction of fibrogenic genes, and repression of COX-2 and IL-1β. CARD-024 treatment did repress the stiffness-induced morphological features including stellate cell morphology and the maturation of focal adhesions. While CARD-024 did not repress pro-fibrotic genes coil A1 and Fn-1, CARD-024 repressed the stiffness-mediated induction of αSMA protein expression, FAK phosphorylation, and MLCK and ET-1 gene expression. In addition, CARD-024 partially stimulated members of the COX-2/IL-1β inflammatory pathway.

CARD-024 attenuated the pro-fibrotic response of colonic myofibroblasts to either TGFβ stimulation or high matrix stiffness, suggesting that CARD-024 and structural analogs can ameliorate intestinal fibrosis.

Although the invention is not limited to any theory, it is considered that 24 ethyl derivatives would have similar biological activity based upon the CARD-024 results with CARD-024. The 24-ethyl substituent is postulated to prevent the normal hepatic 25-hydroxylation, making the 24-ethyl derivatives more hydrophobic than a normal 25 hydroxylated D analog. This would lead to different localization (e.g., membrane vs. cytosol) and different biological activity. The 24-ethyl substituent is the component uniting all the structures herein described for Crohn's and other therapies.

Figure 5:
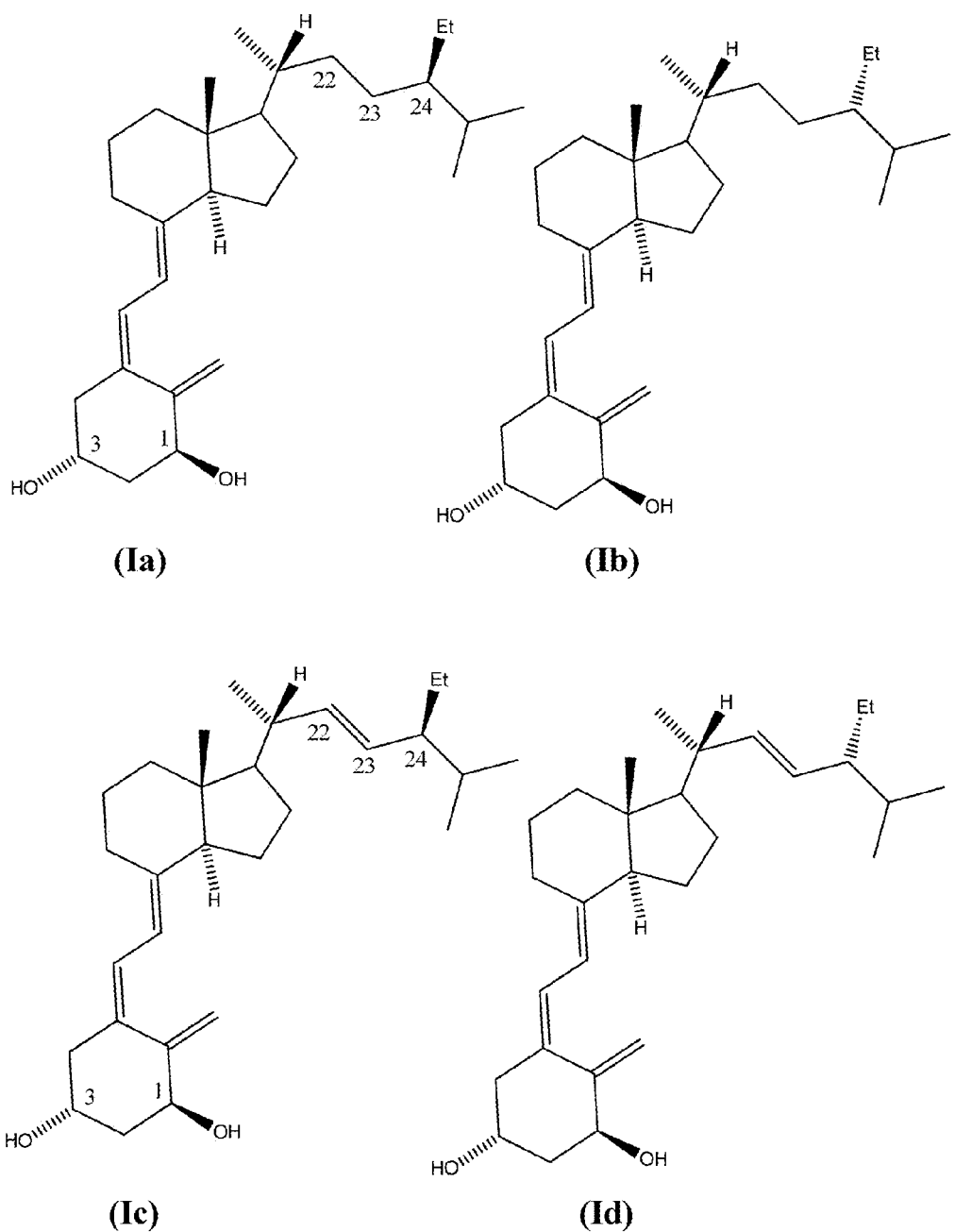
FIG. 5 gives structures of active compounds.

Compounds of Formula (I) are shown in FIG. 5.

Compound Ia is CARD-024, named as (1S,3R)-(5Z,7E)-9,10-Secositosta-5,7,10(19)-triene-1,3-diol.

Compound Ib is 1α-OH-22,23-dihydroporiferacalciferol. It can also be named as (1 S,3R)-(5Z,7E)-9,10-seco-22,23-dihydroporiferasta-5,7,10(19)-triene-1,3-diol.

Compound Ic is 1α-OH-stigma-calciferol. It can also be named as (1 S,3R)-(5Z,7E,22E)-9,10-Secostigmasta-5,7,10(19),22-tetraene-1,3-diol.

Compound Id is 1α-OH-porifera-calciferol. It can also be named as (1S,3R)-(5Z,7E,22E)-9,10-Secoporiferasta-5,7,10 (19),22-tetraene-1,3-diol.

Synthesis of CARD-024 is given for example in Moriarty et al. U.S. Pat. No. 6,900,191, the disclosure of which is hereby incorporated by reference. Other compounds of Formula (I) are made by analogous synthetic routes.

According to any of these embodiments, the composition can be deliverable, for example, by the oral route. Other routes of administration include without limitation parenteral, sublingual, buccal, intranasal, pulmonary, topical, transdermal, intradermal, ocular, otic, rectal, vaginal, intragastric, intracranial, intrasynovial and intra-articular routes. When the subject is able to swallow, it is preferred to provide and administer the compositions in an oral form. These include without limitation tablets, capsules, gel caps, lozenges, and the like.

A composition prepared according to the invention comprises, in addition to the active ingredient selected from among compounds of Formula (I), one or more pharmaceutically acceptable excipients. The excipient or excipients together form a pharmaceutically acceptable carrier.

If the composition is to be prepared in solid form for oral administration, for example as a tablet or capsule, it typically includes at least one or more solid diluents and one or more solid disintegrants. Optionally, the excipients further include one or more binding agents, wetting agents and/or antifrictional agents (lubricants, anti-adherents and/or glidants). Many excipients have two or more functions in a pharmaceutical composition. Characterization herein of a particular excipient as having a certain function, e.g., diluent, disintegrant, binding agent, etc., should not be read as limiting to that function. Depending on the desired dosing scheme, the composition, the carriers provide the dosage form with more or less instantaneous release, or are formulated to give a delayed release or a release spread out over time. The latter are advantageous for patient compliance, as a subject need take fewer doses in a given time. For example, a full daily dose can be provided in an extended release formulation that need be taken only once a day. If desired, the compositions can be provided with enteric coatings that withstand the acid conditions of the stomach, but which release the active ingredient in the more basic confines of the duodenum or small intestine. Further information on excipients can be found in standard reference works such as *Handbook of Pharmaceutical Excipients,* 3rd ed. (Kibbe, ed. (2000), Washington: American Pharmaceutical Association).

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 5% to about 95%, for example about 20% to about 90%, or about 50% to about 85%, by weight of the composition. The diluent or diluents selected preferably exhibit suitable flow properties and, where tablets are desired, compressibility.

Microcrystalline cellulose and silicified microcrystalline cellulose are particularly useful diluents, and are optionally used in combination with a water-soluble diluent such as mannitol. Illustratively, a suitable weight ratio of microcrystalline cellulose or silicified microcrystalline cellulose to mannitol is about 10:1 to about 1:1, but ratios outside this range can be useful in particular circumstances.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.5% to about 20%, or about 1% to about 10%, by weight of the composition.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone or PVP), for example povidone K-15, K-30 and K-29/32; polyacrylic acids (carbomers); polymethacrylates; and the like. One or more binding agents and/or adhesives, if present, typically constitute in total about 0.5% to about 25%, for example about 1% to about 15%, or about 1.5% to about 10%, by weight of the composition.

Povidone and hydroxypropylcellulose, either individually or in combination, are particularly useful binding agents for tablet formulations, and, if present, typically constitute about 0.5% to about 15%, for example about 1% to about 10%, or about 2% to about 8%, by weight of the composition.

Wetting agents, if present, are normally selected to maintain the drug in close association with water, a condition that can improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; tyloxapol; and the like. One or more wetting agents, if present, typically constitute in total about 0.1% to about 15%, for example about 0.2% to about 10%, or about 0.5% to about 7%, by weight of the composition.

Nonionic surfactants, more particularly poloxamers, are examples of wetting agents that can be useful herein. Illustratively, a poloxamer such as Pluronic™ F127, if present, can constitute about 0.1% to about 10%, for example about 0.2% to about 7%, or about 0.5% to about 5%, by weight of the composition.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 5%, or about 0.2% to about 2%, by weight of the composition. Sodium stearyl fumarate is a particularly useful lubricant.

Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.05% to about 10%, for example about 0.1% to about 7%, or about 0.2% to about 5%, by weight of the composition. Colloidal silicon dioxide is a particularly useful anti-adherent.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.05% to about 10%, for example about 0.1% to about 7%, or about 0.2% to about 5%, by weight of the composition. Colloidal silicon dioxide is a particularly useful glidant.

Other excipients such as buffering agents, stabilizers, antioxidants, antimicrobials, colorants, flavors and sweeteners are known in the pharmaceutical art and can be used in compositions of the present invention. Tablets can be uncoated or can comprise a core that is coated, for example with a nonfunctional film or a release-modifying or enteric coating. Capsules can have hard or soft shells comprising, for example, gelatin (in the form of hard gelatin capsules or soft elastic gelatin capsules), starch, carrageenan and/or HPMC, optionally together with one or more plasticizers.

A solid orally deliverable composition of the present invention is not limited by any process used to prepare it. Any suitable process of pharmacy can be used, including dry blending with or without direct compression, and wet or dry granulation.

If the composition is to be prepared in liquid (including encapsulated liquid) form, the active ingredient (a compound according to Formula I) can be, for example, dissolved in a suitable carrier, typically one comprising a lipid solvent for the API. The higher the unit dose, the more desirable it becomes to select a carrier that permits a relatively high concentration of the drug in solution therein. In various embodiments, the concentration of active ingredient in the carrier is at least about 10 mcg/ml (mcg stands for micrograms), e.g., about 10 to about 500 mcg/ml, but lower and higher concentrations can be acceptable or achievable in specific cases. Illustratively, the drug concentration in various embodiments is at least about 10 mcg/ml, e.g., about 10 to about 250 mcg/ml, or at least about 20 mcg/ml, e.g., about 20 to about 200 mcg/ml, for example about 20, about 25, about 30, about 40, about 50, about 75, about 100 or about 150 mcg/ml.

The subject can be human or non-human (e.g., a farm, zoo, work or companion animal, or a laboratory animal used as a model) but in an important embodiment the subject is a human patient in need of the drug, for example to treat a disease characterized by fibrosis, especially of the bowel as in inflammatory bowel disease or Crohn's disease. A human subject can be male or female and of any age, but is typically an adult.

The composition is normally administered in an amount providing a therapeutically effective daily dose of the drug. The term "daily dose" herein means the amount of drug administered per day, regardless of the frequency of administration. For example, if the subject receives a unit dose of 150 mcg twice daily, the daily dose is 300 mcg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the bioavailability of the particular formulation, the subject (including species and body weight of the subject), the disease to be treated, the stage and/or severity of the disease, the individual subject's tolerance of the compound, whether the compound is administered in monotherapy or in combination with one or more other drugs, and other factors. Thus, the daily dose can vary within wide margins, for example from about 10 to about 1000 mcg. Based on body weight, the human effective dose is expected to be on the order of 0.2 to 5 mcg per kilogram of body weight (0.2-5 mcg/kg), for example in the range of 0.5-2 mcg/kg. In a non-limiting illustration, the effective dose is on the order of 25-150 mcg per subject, assuming body weights of 50-150 kilograms. Greater or lesser daily doses can be appropriate in specific situations, and the physician will vary the dosage and titrate the effective amount according to best medical judgment. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating bowel disease, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a patient on a course of therapy with a relatively low daily dose and titrate the dose upwards over a period of days or weeks, to reduce risk of adverse side-effects.

Illustratively, suitable doses of CARD-024 are generally about 10 to about 500 mcg, about 10 to about 250 mcg, about 25 to about 400 mcg, about 25 to about 200 mcg, for example about 5, about 10, about 20, about 25, about 50, about 75, about 100, about 150, about 175, about 200, about 250, about 500, about 750 or about 1000 mcg, administered as needed at an average dosage interval of about 3 hours to about 7 days, for example about 8 hours to about 3 days, or about 12 hours to about 2 days. In most cases a once-daily (q.d.) administration regimen is suitable.

An "average dosage interval" herein is defined as a span of time, for example one day or one week, divided by the number of unit doses administered over that span of time. For example, where a drug is administered three times a day, around 8 am, around noon and around 6 μm, the average dosage interval is 8 hours (a 24-hour time span divided by 3). If the drug is formulated as a discrete dosage form such as a tablet or capsule, a plurality (e.g., 2 to about 10) of dosage forms administered at one time is considered a unit dose for the purpose of defining the average dosage interval.

If desired, one or more agents typically used to treat inflammatory bowel disease may be used in a combination therapy along with a compound or mixture of compounds of Formula I in the methods and compositions of the invention. In various embodiments, methods of treating IBD and CD include administering a composition containing one or more compounds of Formula I and further containing additional active agents. Non-limiting examples of such agents include biologics (e.g., inflixamab, adelimumab, and CDP-870), an immunomodulatory compound such as interleukin-10, interleukin-4, or a TNFα inhibitor, small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid, mesalamine, sulfasalazine, balsalazide disodium, and olsalazine sodium, methotrexate, azathioprine, and alosetron. Thus, in one embodiment, the invention involves the combination of a compound of Formula I and any of the foregoing agents, and methods of treating inflammatory bowel disease or Crohn's disease by administering them to a subject.

DISCUSSION

Administering compositions comprising compounds of Formula (I) has been demonstrated to be effective at relieving fibrosis and treating the symptoms of inflammatory bowel disease such as, without limitation, Crohn's disease.

Crohn's disease (CD) is characterized by cycles of intestinal inflammation (flares) and mucosal healing. While potent anti-inflammatory therapies reduce inflammation and disease symptoms, the need for anti-fibrotic therapies to prevent the inexorable development of fibrostenotic disease remains (Szabo et al., 2010). Intestinal fibrosis remains a significant serious complication of CD, often culminating in surgical intervention (Van Assche et al., 2010). In addition, patients with CD frequently have vitamin D deficiency, though whether a cause or a consequence of intestinal malabsorption remains open to debate (Harris et al., 2008; Siffledeen et al., 2003). In numerous other organ systems, vitamin D deficiency is associated with fibrosis. Treatment with vitamin D analogs reduces fibrosis both in cell culture and in animal models of fibrosis, suggesting that treatment with vitamin D analogs could reduce intestinal fibrosis (Li et al., 2005; Mancuso et al., 2008; Tan et al., 2006; Weishaar et al., 1990; Zhang et al., 2010).

In the intestine, subepithelial myofibroblasts contribute to intestinal wound healing in part by reconstituting the ECM while aberrant myofibroblast activation is postulated to produce fibrosis (Powell et al., 1999; Pucilowska et al., 2000). In CD, activated or dysregulated intestinal myofibroblasts are the major source of excessive ECM and subsequent fibrosis (Powell et al., 1999).

As seen in primary intestinal myofibroblasts (Brenmoehl et al., 2009; Simmons et al., 2002), TGFβ stimulation of human colonic myofibroblast Ccd-18co cells induced a pro-fibrotic phenotype, characterized by increased αSMA protein expression, actin stress fibers, and mature focal adhesions. As disclosed herein, co-treatment with CARD-024, a compound with little hypercalcemic effect, reduced αSMA stimulation by TGFβ in a dose-dependent manner. CARD-024 treatment repressed the gene expression of endothelin-1 which is involved in myofibroblast differentiation and fibrosis (Guidry and Hook, 1991).

In the matrix stiffness model, human colonic myofibroblasts demonstrated morphological changes when cultured on collagen-coated polyacrylamide gels of increasing matrix stiffness. CARD-024 treatment attenuated morphological changes induced by high matrix substrates, including the organization of actin stress fibers, development of mature focal adhesions, and elongated dendritic processes. Actin stress fiber assembly is regulated by MLCK (Anderson et al., 2004). In colonic myofibroblasts, MLCK was transcriptionally induced by high matrix stiffness but repressed by CARD-024, suggesting that the morphological effects of CARD-024 occur through interruption of MLCK-mediated actin assembly.

Activated myofibroblasts are characterized by the expression of αSMA (Powell et al., 1999). Recent work in pulmonary, hepatic, and dermal myofibroblasts demonstrated that a stiff extracellular matrix induces a pro-fibrotic, activated phenotype characterized by increased αSMA expression (Jones and Ehrlich, 2011; Liu et al., 2010; Olsen et al., 2011). In colonic myofibroblasts, high matrix stiffness induced αSMA protein expression while treatment with CARD-024 blocked induction of αSMA protein expression.

Myofibroblast differentiation is (in part) dependent on FAK (focal adhesion kinase) signaling (Brenmoehl et al., 2009). FAK is a critical mediator of cytoskeletal responses including proliferation, migration, and adhesion. (Schaller, 2010) In addition, FAK mediates mechanosensing of the extracellular environment via an integrin signaling pathway (Assoian and Klein, 2008; Parsons, 2003). In colonic myofibroblasts, high matrix stiffness induced pFAK while CARD-024 repressed FAK activation suggesting that CARD-024 may inhibit pFAK signaling. Endothelin-1 (ET-1), a soluble fibrogenic peptide, has been shown to phosphorylate FAK in fibroblasts (Daher et al., 2008; Kennedy et al., 2008) while vitamin D antagonizes ET-1 stimulation in cardiac myocytes (Wu et al., 1996). In our stiffness model, ET-1 transcription is induced by high matrix stiffness and repressed by CARD-024, suggesting that vitamin D analogs may target the FAK/ET-1 pathway. However, CARD-024 treatment did not repress the expression of the classic fibrogenic genes colA1 and Fn-1. Collagen expression is regulated in part by both extra- and intracellular calcium levels (Fitzgerald et al., 2006; Nakade et al., 2001). CARD-024 has minimal effects on calcium metabolism, therefore failure to repress collagen gene expression may due to the calcium-mediated regulation of collagen gene expression Vitamin D and its metabolites have been reported to repress or induce fibronectin expression, depending on the cell type (Ezzat and Asa, 2005; Ramirez et al., 2010). Fibronectin expression is necessary for cell adhesion and attenuation of fibronectin expression may reduce cellular responsiveness to vitamin D or its analogs (Ezzat and Asa, 2005).

Recently, the COX-2/PGE2 pathway has been described as mediating the pro-fibrotic response to matrix stiffness (Liu et al., 2010). Though our work did not conclusively demonstrate that high matrix stiffness represses COX-2/PTGS2 in colonic myofibroblasts, a repressive trend was observed in high matrix stiffness while CARD-024 treatment showed a stimulatory trend in both low and high matrix stiffness's. While the mechanism of matrix stiffness regulation of COX-2 is unknown, COX-2 expression in intestinal myofibroblasts is regulated by IL-1β (Hinterleitner et al., 1996). In colonic myofibroblasts cultured on low or high stiffness matrices, IL-1β is transcriptionally repressed by high stiffness. In macrophages, vitamin D (1,25-Dihydroxyvitamin D3 (1,25(OH)2D3), stimulates IL-1β in macrophages. (Lee et al., 2011) CARD-024 markedly induced IL-1β expression irrespective of matrix stiffness, suggesting CARD-024 may target an IL-1β/COX-2 pathway.

Intestinal fibrosis and vitamin D deficiency are two frequent complications of Crohn's disease. The high proportion of CD patients ultimately requiring surgical intervention underscores the need for effective anti-fibrotic medical therapies. This study demonstrates that CARD-024, a compound with minimal hypercalcemic effects, reduces the fibrogenic response of intestinal myofibroblasts.

These results support monitoring and maintaining normal vitamin D levels in Crohn's disease patients with a history of fibrostenotic disease.

EXAMPLES

Human recombinant TGFβ1 was obtained from R&D Systems (Minneapolis, Minn.). CARD-024 (1-alpha-hydroxyvitamin D5) was provided by R. Simpson (Cardiavent Inc., Ann Arbor, Mich.) and dissolved in 100% ethanol. All chemicals were purchased from Sigma (Sigma-Aldrich, Saint Louis, Mo.), except where noted.

Cell Culture

Colonic human myofibroblast Ccd-18co cells (CRL-1459 from ATCC) were cultured in alpha-MEM (Invitrogen, Carlsbad, Calif.) supplemented with 10% fetal bovine serum and sub-cultured weekly.

Cells were plated at 30-40% confluence. To stimulate a fibrotic phenotype, Ccd-18co cells were serum-starved for 24 h prior to treatment with 1 ng/ml TGFβ or 1 ng/ml TGFβ and increasing doses of CARD-024 (10-1000 nM) for 48 h. Given ethanol was used to dilute CARD-024, ethanol was added to the untreated and TGFβ treated cells to a final concentration of 0.1%. For stiffness experiments, low-passage number Ccd-18co cells were seeded at 1×105 cells/ml on 6-well plates containing collagen-coated acrylamide gels corresponding to soft (4.3 kPa, 0.02% bisacrylamide) or stiff (28.1 kPa, 0.16%) matrices. Cells were allowed to attach to the matrix for 4 h and then the gels were transferred to new wells to avoid paracrine signaling from cells attached to the plastic well bottom. For the CARD-024 stiffness experiments, cells were plated as described above and serum-starved overnight prior to treatment with 1000 nM of CARD-024 diluted in 100% ethanol for 24 h. The 1000 nM CARD-024 dose was selected from the results of the TGFβ experiments. Since ethanol was used to dilute CARD-024, ethanol was added to untreated cells to a final concentration of 0.1%.Experiments were performed on early (4 to 7) passage cells. Cultures were routinely assayed for mycoplasma contamination.

Matrix Stiffness Gels

Collagen-coated polyacrylamide gels corresponding to physiological stiffnesses of 2.6 kPa to 28.1 kPa were generated using varying ratios of 40% acrylamide to 2% bisacrylamide (Bio-Rad, Hercules, Calif.) (Aplin and Hughes, 1981; Pelham and Wang, 1998). Specifically, an aqueous solution of 0.10% ammonium persulfate (Bio-Rad), 0.15% TEMED (Bio-Rad), 40% acrylamide solution was supplemented with 0.01%, 0.02%, 0.08%, or 0.16% bisacrylamide. The acrylamide gels were polymerized on a NaOH treated, amino-silanated (3-aminopropyltriethoxysilane), and glutaraldehyde treated 25 mm round glass coverslip. 10 ml of each acrylamide/bisacrylamide solution was filter sterilized and pipetted unto a chloro-silanated glass surface treated with dichlorodimethylsilane (DCDMS) and a treated coverslip was inverted onto the acrylamide/biacrylamide solution. The acrylamide matrix was allowed to polymerize for 10 min between the two surfaces and transferred to a 6-well tissue culture plate containing sterile PBS. As determined by a series of stability experiments (data not shown), the acrylamide gels were stable for at least 1 month. For all experiments, gels were used within a month.

Prior to seeding with colonic myofibroblasts, the acrylamide gels were collagen-coated. 0.2 mg/ml of sulfo-SANPAH (Thermo Scientific, Rockford, Ill.) was added to each well containing the acrylamide gel-coated cover slip and UV crosslinked at a wavelength of 254 nm in a Stratagene UV crosslinker oven (Stratagene, La Jolla, Calif.) at a 5-inch distance from the UV source for 10 min. The gels were coated with 0.2 mg/ml of rat tail collagen I (BD Biosciences, Bedford, Mass.) overnight at 37° C. with gentle agitation. Excess collagen was removed by several washes with sterile PBS. Gels were UV sterilized for 30 min prior to seeding with colonic myofibroblasts. Cells were serum-starved overnight prior to treatment with CARD-024. From the results of the TGFβ treatment experiments, 1000 nM CARD-024 was selected for all stiffness matrix experiments.

Control cells received ethanol at the same final concentration (0.1%) to control for the ethanol concentration in CARD-024 solution.

Microelastometer Measurements

Microelastometer measurements were determined for acrylamide/bisacrylamide gels ranging from 2.6 to 28.1 kPa bisacrylamide using a microelastometer (Micro-Elastometer, Artann Laboratories, West Trenton, N.J.) (Egorov et al., 2008). For the microelastometer measurements, gels were synthesized without a NaOH-treated glass coverslip.

For measurements, thicker gels were used than for cell plating since previous experiments determined a larger material height (substrate thickness) was needed to generate accurate and reproducible microelastomer measurements (data not shown).

By measuring vertical displacement of the gels, the stress (force per unit area) and strain (material compression in response to force) were determined by the microelastometer. Raw stress and strain values were plotted and the slope of the stress-strain curve was determined using the region between the first and second points of inflection to calculate the Young's Modulus (kPa), an expression of substrate stiffness.

Protein Isolation and Western Blotting

Immunoblotting was utilized for the detection of α-smooth muscle actin. Ccd-18Co cells were washed in ice-cold PBS containing protease inhibitors (Roche, Indianapolis, Ind.), then lysed in ice-cold RIPA buffer (1% Igepal CA 630, 1% sodium deoxycholate, 0.1% SDS, 0.15 M NaCl, 2 mM EDTA, 50 mM NaF) with a 1:100 dilution of protease inhibitor cocktail III (Calbiochem, La Jolla, Calif.) and 2 mM sodium orthovanadate.

Total protein was separated by SDS polyacrylamide gel electrophoresis (Bio-Rad,) with prestained protein markers loaded for molecular mass determination (Invitrogen, Carlsbad, Calif.), and transferred to PVDF membranes (Amersham Biosciences, Piscataway, N.J.). Membranes were blocked in 5% milk/TBST solution for 1 h at room temperature or overnight at 4° C. α-smooth muscle actin was detected by incubating the membrane overnight at 4° C. with mouse anti-human monoclonal antibody (Sigma, St. Louis, Mo.) at 1:5000 dilution in 5% milk/TBST.

pFAK was detected using a rabbit polyclonal phospho-specific antibody against Tyr-397-FAK (Invitrogen) at 1:5000. As a loading control, a mouse antibody for GAPDH (Chemicon, Temecula, Calif.) was used. After washing, the membranes were incubated with the appropriate secondary antibody (anti-mouse IgG+HRP or anti-rabbit IgG+HRP, Amersham, Piscataway, N.J.) for 1 h at room temperature and the signal was detected by the Pierce detection system (Pierce, Rockford, Ill.). Autoradiographs were scanned and quantitated using ImageJ analysis software (NIH, Bethesda, Md.).

Microscopy

Cells were photographed using a Leica (Leica Microsystems Inc., Buffalo Grove, Ill.) DMIRB inverted microscope and photographed with an Olympus DP-30 camera (Center Valley, Pa.). Cell length was determined from photomicrographs using ImageJ (NIH, Bethesda, Md.). Cell count was determined from a minimum of 3 representative photographs of a 100× magnification field.

Immunofluorescence

Expression of activated myofibroblast markers was analyzed by confocal immunofluorescence microscopy using the Olympus FluoView™ FV500/IX system (Olympus America, Center Valley, Pa.) at the University of Michigan Microscopy and Image Analysis Laboratory. Ccd-18Co cells were seeded onto collagen-coated polyacrylamide gels (0.02% bis or 0.16% bis) attached to glass coverslips. After 24 h, gels were rinsed with PBS, then were fixed with 4% paraformaldehyde (Electron Microscopy Sciences, Hatfield, Pa.) in PBS for 5 min, followed by permeabilization with 0.2% Triton X-100 (LabChem, Pittsburgh, Pa.) for 15 min. Gels were rinsed 3 times with PBS, then were pre-blocked with SFX signal enhancer (Invitrogen, Carlsbad, Calif.), and blocked with 20% goat serum (Invitrogen, Carlsbad, Calif.).

For visualization of focal adhesions, the gels were incubated for 2 h at room temperature with mouse anti-vinculin primary antibody (Sigma, St. Louis, Mo.) at 1:250 in PBS/0.1% Triton X-100. The gels were rinsed three times with PBS/0.1% Triton-X100, followed by incubation with Alexa 555-conjugated goat anti-mouse secondary antibody (Molecular Probes, Eugene, Oreg.) for 30 min, at room temperature, in PBS/0.1% Triton X-100. Gels were washed 6 times, followed by incubation with phalloidin (Sigma, St. Louis, Mo.) at 1:100, overnight, at 4° C., for visualization of actin stress fibers. Cells were co-stained with 4,6'-diamidino-2-phenylindole (DAPI), (Molecular Probes, Eugene, Oreg.) to visualize nuclei. The gels were mounted with ProLong Gold mounting medium (Invitrogen, Carlsbad, Calif.) prior to imaging by confocal immunofluorescence microscopy.

Quantitative RT-PCR

RNA from Ccd-18co cells was extracted using the RNeasy kit (Qiagen, Valencia, Calif.). cDNA was generated by reverse transcription of 1 µg of total RNA using the Superscript First Strand RT kit (Invitrogen, Carlsbad, Calif.). Quantitative real-time PCR (qPCR) was performed for MLCK, IL-1β, PTGS2, ET-1, and GAPDH with the TaqMan gene expression assays (ABI, Foster City, Calif.) on a Bio-Rad iCycler real-time PCR system. Cycling conditions were 95° C. 10 min, followed by 40 cycles of 95° C. 15 s and 62° C. 60 s. Gene expression was normalized to GAPDH as the endogenous control, and fold-changes (RQ) relative to untreated controls were calculated using the LACt-method (Livak and Schmittgen, 2001).

Statistical Analysis

Comparisons between multiple were analyzed with ANOVA, while pairwise comparisons of two groups were performed with Student's t test.

Results

Example 1

Dose Response of Colonic Myofibroblasts to CARD-024

To induce a pro-fibrotic phenotype, human colonic myofibroblasts (Ccd-18co cells) were treated with increasing doses of TGFβ1 (0.1-2 ng/ml). Consistent with (Simmons et al., 2002), TGFβ induced a pro-fibrotic response as characterized by a dose-dependent increase in αSMA protein expression (FIG. 1A) and increased actin stress fiber and focal adhesion staining (data not shown).

To determine whether CARD-024 represses fibrogenesis in colonic myofibroblasts, Ccd-18co cells were stimulated with TGFβ and treated with 10-1000 nM CARD-024 (FIG. 1B). In colonic myofibroblasts stimulated with TGFβ, increasing doses of CARD-024 attenuated αSMA protein expression in a dose-responsive manner. At the highest dose (1000 nM) CARD-024 attenuated αSMA protein expression 2-fold (p=0.012) (FIG. 1C).

Example 2

Development of Collagen-Coated Polyacrylamide Gels

Typical culture of lung myofibroblasts on rigid plastic substrates has profound effects on myofibroblast differentiation and activation (Hinz, 2010). In lung myofibroblasts, matrix stiffness induces changes in cell phenotype and function from a quiescent, non-proliferative phenotype to an activated, ECM-secreting phenotype (Hinz, 2010).

Given that CARD-024 repressed αSMA protein expression on the rigid plastic matrix, we postulated that CARD-024 might have an anti-fibrotic effect on colonic myofibroblasts cultured on a more physiologically compliant substrate.

To determine the effect of matrix stiffness on colonic myofibroblast phenotype, collagen-coated polyacrylamide gels were generated as detailed in the Experimental Procedures. Varying the ratio of acrylamide to bisacrylamide from 0.01% to 0.16% produced substrates with stiffnesses from 2.6 to 28.1 kPa as determined by microelastometer measurements.

Figure 2:
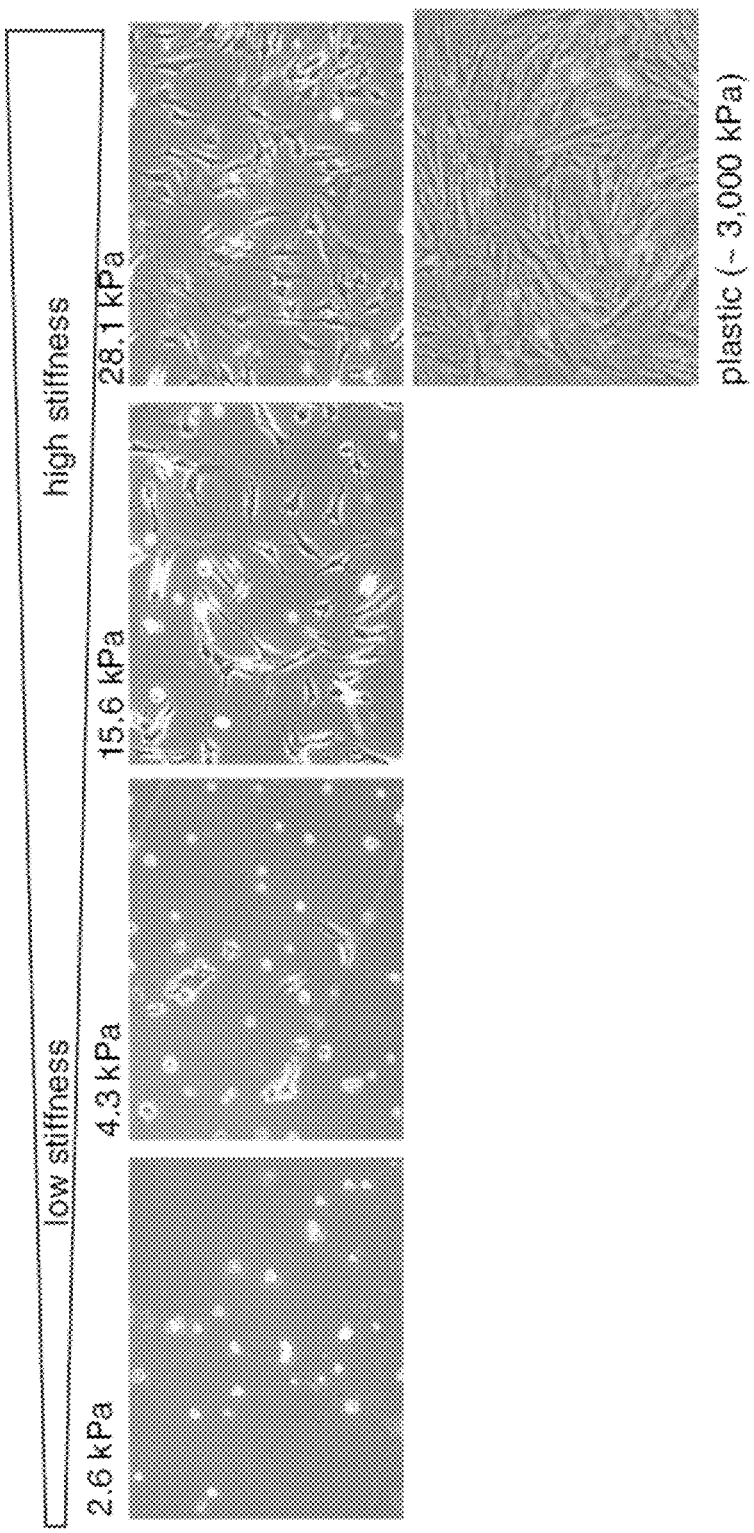
FIG. 2—Effect of increasing matrix stiffness on myofibroblast phenotype. Brightfield photomicrographs of colonic myofibroblasts cultured on substrates of increasing matrix stiffness of 0.01% (2.6 kPa), 0.02% (4.3 kPa), 0.08% (15.6 kPa), and 0.16% (28.1 kPa). Myofibroblasts cultured on a standard plastic substrate are shown for comparison.

Similar to published work in myofibroblasts from other tissues, Ccd-18co colonic myofibroblasts cultured on these matrices demonstrated a graded monotonic change in morphology with increasing matrix stiffness. On low stiffness substrates (2.6 and 4.3 kPa), cells exhibited an undifferentiated phenotype, characterized by a rounded appearance, with a few cells displaying small dendritic processes. However the dendritic processes were markedly truncated and less numerous compared to the typical myofibroblast morphology on the plastic substrate (FIG. 2). In contrast, cells cultured on the high stiffness substrates (15.6 and 28.1 kPa) exhibited a more differentiated morphology, with a characteristic stellate appearance and multiple, elongated dendritic processes resembling myofibroblasts cultured on plastic. Compared to cells cultured on the low matrix stiffness, myofibroblasts cultured on the high stiffness substrates had more actin stress fiber staining with mature focal adhesions apparent in the highest matrix stiffness (data not shown).

Example 3

Effects of CARD-024 and Substrate Stiffness on Myofibroblast Morphology

To determine whether CARD-024 altered myofibroblast morphology, we analyzed the effect of CARD-024 treatment on colonic myofibroblasts cultured on low (4.3 kPa) and high (28.1 kPa) stiffness substrates. For the low stiffness substrate, 4.3 kPa gels were selected as the 2.6 kPa gels proved difficult to image by confocal microscopy.

Figure 3:
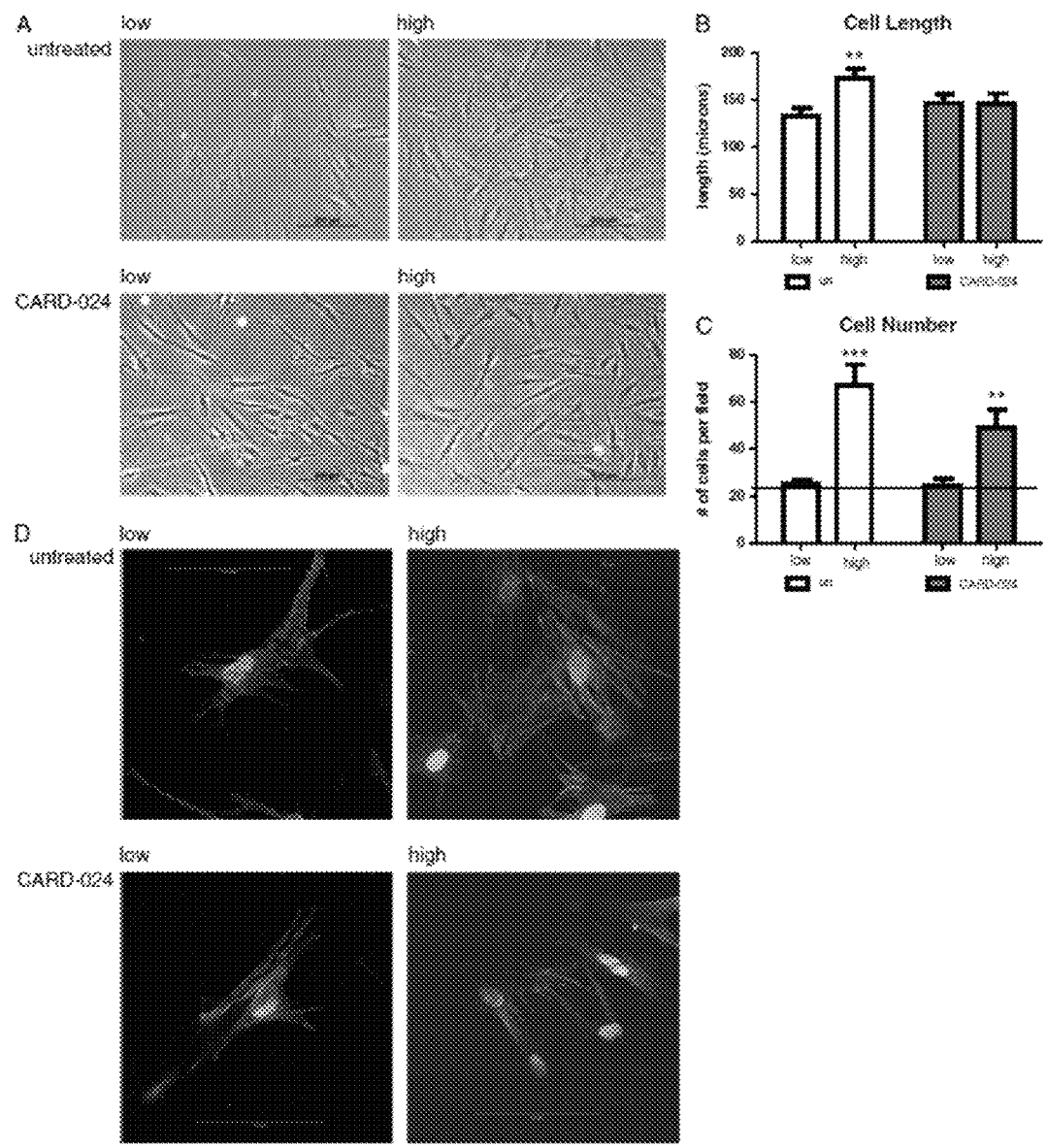
FIG. 3—Effect of CARD-024 and matrix substrate stiffness on cell morphology and growth in colonic myofibroblasts. (A) Phase-contrast micrographs of untreated myofibroblasts (upper panel) on low and high matrix stiffness compared to myofibroblasts treated with 1000 nM CARD-024 at low and high stiffness (lower panel). 100× magnification. (B) Cell length of untreated (white bars) compared to CARD-024 treated cells (dark bars) on low or high stiffness matrices. (C) Cell density counts of untreated myofibroblasts (white bars) compared to CARD-024 (dark bars) on low or high stiffness matrices. The horizontal reference line denotes baseline (untreated) expression. Asterisks denote statistically significant comparisons between untreated/low stiffness and other experimental groups. p<0.01, *p<0.001 (D) Confocal micrographs of myofibroblasts on low or high matrix substrates treated with 1000 nM CARD-024 compared to untreated cells using Alexa 555-conjugated vinculin (red) and phalloidin (green). Nuclei were visualized by DAPI (blue). The scale bar represents 100 μm.

Ccd-18co cells cultured on the high stiffness (28.1 kPa) matrix developed a stellate morphology, with multiple dendritic processes compared to myofibroblasts grown on the low stiffness (4.3 kPa) matrix (FIG. 3B). Similar to human foreskin fibroblasts, which develop elongated dendritic processes in response to increase matrix stiffness (Jones and Ehrlich, 2011), colonic myofibroblasts on the stiff substrate had significantly elongated dendritic processes compared to myofibroblasts cultured on the soft substrate (173 µm vs 133 µm, p=0.004)(FIG. 3C). High matrix stiffness also increased the number of cells >2.5-fold compared to the soft matrix (66.5 vs 25 cells/200×field, p=0.0043) (FIG. 3D).

Treatment with CARD-024 repressed the effects of matrix stiffness on cell morphology, with cell morphology on the high stiffness substrates in the presence of CARD-024 that was quite similar to the myofibroblasts on low stiffness substrates (FIG. 3B). Dendrite length was nearly identical (146 vs 145 µm, p=0.95) between CARD-024 treated myofibroblasts on low compared to high stiffness matrices (FIG. 3C). While treatment with CARD-024 did not significantly decrease the number of myofibroblasts on the stiff substrate, a 50% reduction in cell number was observed compared to untreated cells on the stiff matrix, suggesting a non-significant trend toward decreased cell number with CARD-024 treatment.

Activated myofibroblasts are characterized by the development of actin stress fibers and focal adhesions (Hinz, 2010). Colonic myofibroblasts cultured on the soft substrate had fewer actin stress fibers and diffuse vinculin staining without organized focal adhesions (FIG. 3D). In contrast, myofibroblasts cultured on the stiff matrix exhibited an activated morphology with increased numbers of actin stress fibers and mature, well-defined focal adhesions (FIG. 3D). On the stiff substrate, treatment with CARD-024 produced poorly organized immature focal adhesions with diffuse cytoplasmic staining, suggesting CARD-024 inhibited focal adhesion maturation (FIG. 3D).

Example 4

Effect of CARD-024 and Substrate Stiffness on ECM Protein and Gene Expression

Figure 4:
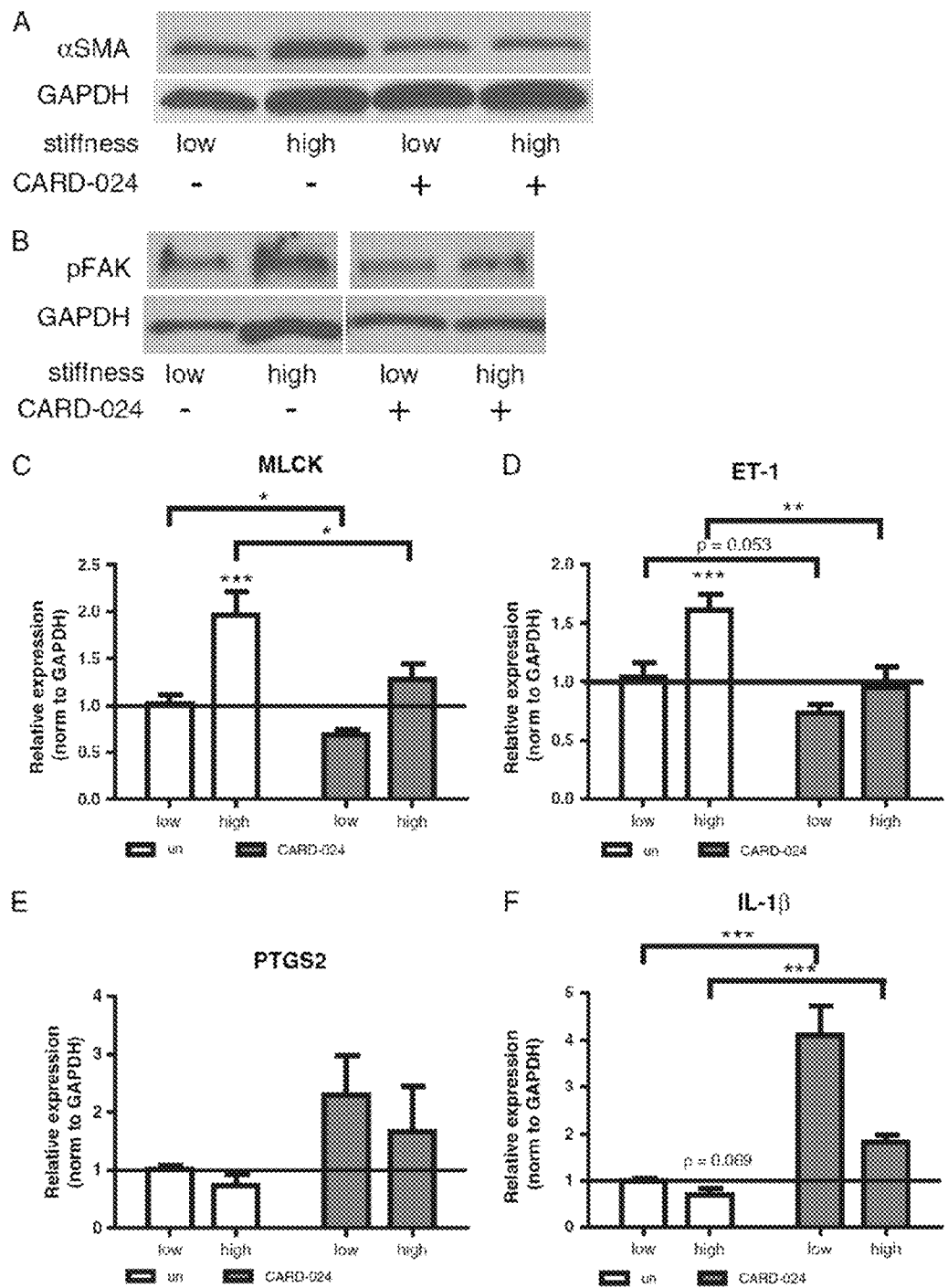
FIG. 4—Effect of CARD-024 and substrate stiffness ECM protein and gene expression. (A) Representative Western of αSMA protein expression in untreated or CARD-024 treated colonic myofibroblasts on low or high stiffness substrates. (B) Representative Western of pFAK protein expression in untreated or CARD-024 treated colonic myofibroblasts on low or high stiffness substrates. In (A) and (B) GAPDH protein expression is used as a control for protein loading. (CH) QRT-PCR expression of fibrogenic (MLCK (C), ET-1 (D) or COX-2 pathway (PTGS2 (E), IL-1β(F)) genes in colonic myofibroblasts cultured on low or high stiffness substrates treated with CARD-024 (dark bars) compared to untreated cells (white bars). Asterisks denote comparisons between untreated/low stiffness and other groups. The horizontal reference line denotes baseline (untreated/low stiffness) expression. Pairwise comparisons between groups are denoted with brackets. *p<0.05, p<0.01, *p<0.001.

Similar to the pro-fibrotic effects of TGFβ stimulation, high matrix stiffness induced αSMA protein expression in colonic myofibroblasts (FIG. 4A). Treatment with CARD-024 repressed αSMA expression on the high stiffness substrate to levels indistinguishable from the low stiffness substrate. Myofibroblast differentiation and cytoskeletal reorganization is dependent upon a number of factors, including FAK (focal adhesion kinase) signaling (Brenmoehl et al., 2009). In colonic myofibroblasts, the high stiffness matrix induced phosphorylation of focal adhesion kinase (FAK), while CARD-024 inhibited FAK phosphorylation, suggesting CARD-024 affects pFAK signaling (FIG. 4B).

Actin stress fiber formation is regulated in part by myosin light chain kinase (MLCK) (Anderson et al., 2004). Given that CARD-024 repressed the development of actin stress fibers and mature focal adhesions, we examined the role of matrix stiffness and CARD-024 upon MLCK gene expression. MLCK was induced 2-fold (p=0.004) in myofibroblasts on the high compared to a low stiffness substrate (FIG. 4C). Treatment with CARD-024 significantly repressed MLCK expression to levels comparable to untreated cells on the low stiffness substrate (FIG. 4C).

Similarly, the high stiffness substrate significantly induced ET-1 gene expression by 60% (p=0.009) (FIG. 4D). Treatment with CARD-024 significantly repressed ET-1 expression in high stiffness conditions to levels indistinguishable from low stiffness conditions.

In pulmonary myofibroblasts, matrix stiffness suppresses an endogenous COX-2/PGE2 inhibitory pathway (Liu et al., 2010). While increased matrix stiffness attenuated but did not significantly repress PTGS2 (which encodes the COX-2 enzyme), treatment with CARD-024 induced PTGS2 at both low and high stiffness, suggesting CARD-024 may affect the COX-2/PGE2 pathway (FIG. 4E). In intestinal myofibroblasts, IL-1β stimulates COX-2 expression (Hinterleitner et al., 1996). Therefore we examined the effect of matrix stiffness and CARD-024 on IL-1β expression.

High matrix stiffness attenuated IL-1β expression, though this did not achieve statistical significance (p=0.069). Treatment with CARD-024 significantly induced IL-1β expression above low stiffness levels with a 4-fold induction at low stiffness (pb0.0001) and 1.8-fold induction at high stiffness (p=0.002) (FIG. 4F).

REFERENCES

Anderson, S., DiCesare, L., Tan, I., Leung, T., Sundar Raj, N., 2004. Rho-mediated assembly of stress fibers is differentially regulated in corneal fibroblasts and myofibroblasts. Experimental Cell Research 298, 574-583.

Andres, P. G., Friedman, L. S., 1999, Epidemiology and the natural course of inflammatory bowel disease. Gastroenterology Clinics of North America 28, 255-281 vii.

Aplin, J. D., Hughes, R. C., 1981, Protein-derivatised glass coverslips for the study of cell to substratum adhesion. Analytical Biochemistry 113, 144-148.

Arora, P. D., Narani, N., McCulloch, C. A., 1999. The compliance of collagen gels regulates transforming growth factor-beta induction of alpha-smooth muscle actin in fibroblasts. The American Journal of Pathology 154, 871-882.

Assoian, R. K., Klein, E. A., 2008. Growth control by intracellular tension and extracellular stiffness. Trends in Cell Biology 18, 347-352.

Brenmoehl, J., Miller, S. N., Hofmann, C., Vogl, D., Falk, W., Scholmerich, J., Rogler, G., 2009. Transforming growth factor-beta 1 induces intestinal myofibroblast differentiation and modulates their migration. World Journal of Gastroenterology 15, 1431-1442.

Cosnes, J., Cattan, S., Blain, A., Beaugerie, L., Carbonnel, F., Parc, R., Gendre, J. P., 2002. Long-term evolution of disease behavior of Crohn's disease. Inflammatory Bowel Diseases 8, 244-250.

Daher, Z., Noel, J., Claing, A., 2008. Endothelin-1 promotes migration of endothelial cells through the activation of ARF6 and the regulation of FAK activity. Cellular Signalling 20, 2256-2265.

Egorov, V., Tsyuryupa, S., Kanilo, S., Kogit, M., Sarvazyan, A., 2008. Soft tissue elastometer, Medical Engineering & Physics 30, 206-212.

L. A. Johnson et al./Experimental and Molecular Pathology 93 (2012) 91-98 97.

Ezzat, S., Asa, S. L., 2005. The molecular pathogenetic role of cell adhesion in endocrine neoplasia. Journal of Clinical Pathology 58, 1121-1125.

Fitzgerald, J. B., Jin, M., Grodzinsky, A. J., 2006. Shear and compression differentially regulate clusters of functionally related temporal transcription patterns in cartilage tissue. The Journal of Biological Chemistry 281, 24095-24103.

Guidry, C., Hook, M., 1991. Endothelins produced by endothelial cells promote collagen gel contraction by fibroblasts, The Journal of Cell Biology 115, 873-880.

Harries, A. D., Brown, R., Heatley, R. V., Williams, L. A., Woodhead, S., Rhodes, J., 1985. Vitamin D status in Crohn's disease: association with nutrition and disease activity, Gut 26, 1197-1203.

Harris, P. R., Wright, S. W., Serrano, C., Riera, F., Duarte, I., Torres, J., Pena, A., Rollan, A., Viviani, P., Guiraldes, E., Schmitz, J. M., Lorenz, R. G., Novak, L., Smythies, L. E., Smith, P. D., 2008. Helicobacter pylori gastritis in children is associated with a regulatory T-cell response. Gastroenterology 134, 491-499.

Hinterleitner, T. A., Saada, J. I., Berschneider, H. M., Powell, D. W., Valentich, J. D., 1996. IL-1 stimulates intestinal myofibroblast COX gene expression and augments activation of Cl-secretion in T84 cells, The American Journal of Physiology 271, C1262-C1268.

Hinz, B., 2010. The myofibroblast: paradigm for a mechanically active cell. Journal of Biomechanics 43, 146-155.

Jones, C., Ehrlich, H. P., 2011. Fibroblast expression of alpha-smooth muscle actin, a2β1 integrin and alphav-beta3 integrin: influence of surface rigidity, Experimental and Molecular Pathology 91, 394-399.

Kennedy, L., Shi-Wen, X., Carter, D. E., Abraham, D. J., Leask, A., 2008, Fibroblast adhesion results in the induction of a matrix remodeling gene expression program, Matrix Biology 27, 274-281.

Lee, B. N., Kim, T. H., Jun, J. B., Yoo, D. H., Woo, J. H., Choi, S. J., Lee, Y. H., Song, G. G., Kim, Y., Lee, J. Y., Sohn, J., Ji, J. D., 2011, Upregulation of interleukin-1beta production by 1,25-dihydroxyvitamin D(3) in activated human macrophages. Molecular Biology Reports 38, 2193-2201.

Li, Y., Spataro, B. C., Yang, J., Dai, C., Liu, Y., 2005. 1,25-dihydroxyvitamin D inhibits renal interstitial myofibroblast activation by inducing hepatocyte growth factor expression, Kidney International 68, 1500-1510.

Liu, F., Mih, J. D., Shea, B. S., Kho, A. T., Sharif, A. S., Tager, A. M., Tschumperlin, D. J., 2010, Feedback amplification of fibrosis through matrix stiffening and COX-2 suppression, The Journal of Cell Biology 190, 693-706.

Livak, K. J., Schmittgen, T. D., 2001, Analysis of relative gene expression data using realtime quantitative PCR and the 2(-Delta Delta C(T)) Method. Methods 25, 402-408.

Loftus Jr., E. V., 2004. Clinical epidemiology of inflammatory bowel disease: Incidence, prevalence, and environmental influences, Gastroenterology 126, 1504-1517.

Mancuso, P., Rahman, A., Hershey, S. D., Dandu, L., Nibbelink, K. A., Simpson, R. U., 2008, 1,25-Dihydroxyvitamin-D3 treatment reduces cardiac hypertrophy and left ventricular diameter in spontaneously hypertensive heart failure-prone (cp/+) rats independent of changes in serum leptin. Journal of Cardiovascular Pharmacology 51, 559-564.

Mehta, R. G., Hussain, E. A., Mehta, R. R., Das Gupta, T. K., 2003. Chemoprevention of mammary carcinogenesis by 1alpha-hydroxyvitamin D5, a synthetic analog of Vitamin D. Mutation Research 523-524, 253-264.

Nakade, O., Takahashi, K., Takuma, T., Aoki, T., Kaku, T., 2001, Effect of extracellular calcium on the gene expression of bone morphogenetic protein-2 and -4 of normal human bone cells. Journal of Bone and Mineral Metabolism 19, 13-19.

Olsen, A. L., Bloomer, S. A., Chan, E. P., Gaca, M. D., Georges, P. C., Sackey, B., Uemura, M., Janmey, P. A., Wells, R. G., 2011. Hepatic stellate cells require a stiff environment for myofibroblastic differentiation, American Journal of Physiology, Gastrointestinal and Liver Physiology 301, G110-G118.

Parsons, J. T., 2003, Focal adhesion kinase: the first ten years, Journal of Cell Science 116, 1409-1416.

Pelham Jr., R. J., Wang, Y. L., 1998, Cell locomotion and focal adhesions are regulated by the mechanical properties of the substrate, The Biological Bulletin 194, 348-349 discussion 349-50.

Powell, D. W., Mifflin, R. C., Valentich, J. D., Crowe, S. E., Saada, J. I., West, A. B., 1999, Myofibroblasts, II. Intestinal subepithelial myofibroblasts, The American Journal of Physiology 277, C183-C201.

Pucilowska, J. B., Williams, K. L., Lund, P. K., 2000, Fibrogenesis, IV, Fibrosis and inflammatory bowel disease: cellular mediators and animal models, American Journal of Physiology. Gastrointestinal and Liver Physiology 279, G653-G659.

Rahman, A., Hershey, S., Ahmed, S., Nibbelink, K., Simpson, R. U., 2007, Heart extracellular matrix gene expression profile in the vitamin D receptor knockout mice, The Journal of Steroid Biochemistry and Molecular Biology 103, 416-419.

Ramirez, A. M., Wongtrakool, C., Welch, T., Steinmeyer, A., Zugel, U., Roman, J., 2010, Vitamin D inhibition of pro-fibrotic effects of transforming growth factor beta1 in lung fibroblasts and epithelial cells, The Journal of Steroid Biochemistry and Molecular Biology 118, 142-150.

Schaller, M. D., 2010, Cellular functions of FAK kinases: insight into molecular mechanisms and novel functions. Journal of Cell Science 123, 1007-1013.

Siffledeen, J. S., Siminoski, K., Steinhart, H., Greenberg, G., Fedorak, R. N., 2003, The frequency of vitamin D deficiency in adults with Crohn's disease. Canadian Journal of Gastroenterology 17, 473-478.

Simmons, J. G., Pucilowska, J. B., Keku, T. O., Lund, P. K., 2002. IGF-I and TGF-beta1 have distinct effects on phenotype and proliferation of intestinal fibroblasts, American Journal of Physiology, Gastrointestinal and Liver Physiology 283, G809G818.

Szabo, H., Fiorino, G., Spinelli, A., Rovida, S., Repici, A., Malesci, A. C., Danese, S., 2010, Review article: anti-fibrotic agents for the treatment of Crohn's disease lessons learnt from other diseases, Alimentary Pharmacology & Therapeutics 31, 189-201.

Tan, X., Li, Y., Liu, Y., 2006, Paricalcitol attenuates renal interstitial fibrosis in obstructive nephropathy, Journal of the American Society of Nephrology 17, 3382-3393.

Tomasek, J. J., Gabbiani, G., Hinz, B., Chaponnier, C., Brown, R. A., 2002, Myofibroblasts and mechano-regulation of connective tissue remodeling, Nature Reviews, Molecular Cell Biology 3, 349-363.

Van Assche, G., Vermeire, S., Rutgeerts, P., 2010, The potential for disease modification in Crohn's disease, Nature Reviews, Gastroenterology & Hepatology 7, 79-85.

Weishaar, R. E., Kim, S. N., Saunders, D. E., Simpson, R. U., 1990, Involvement of vitamin D3 with cardiovascular function, III, Effects on physical and morphological properties, The American Journal of Physiology 258, E134E142.

Wu, J., Garami, M., Cheng, T., Gardner, D. G., 1996, 1,25(OH)2 vitamin D3, and retinoic acid antagonize endothelin-stimulated hypertrophy of neonatal rat cardiac myocytes, The Journal of Clinical Investigation 97, 1577-1588.

Zhang, Y., Kong, J., Deb, D. K., Chang, A., Li, Y. C., 2010, Vitamin D receptor attenuates renal fibrosis by suppressing the renin-angiotensin system, Journal of the American Society of Nephrology 21, 966-973.

Zhang, G. Y., Cheng, T., Luan, Q., Liao, T., Nie, C. L., Zheng, X., Xie, X. G., Gao, W. Y., 2011, Vitamin D: a novel therapeutic approach for keloid, an in vitro analysis, The British Journal of Dermatology 164, 729-737.

We claim:

1. A method of ameliorating intestinal fibrosis in a subject, the method comprising administering to the subject a composition comprising a compound of Formula (I)

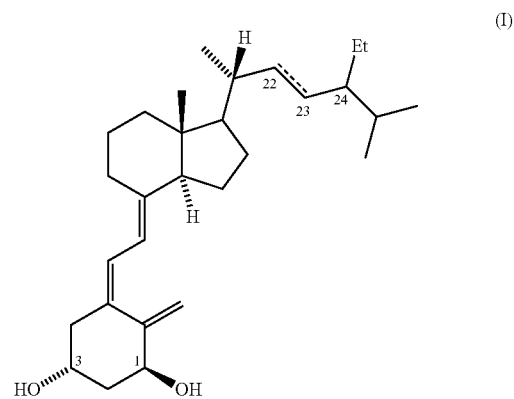

wherein Et is ethyl, wherein the dashed line indicates a single bond or a double bond in the E configuration between carbon 22 and carbon 23, and wherein the configuration at carbon 24 to which Et is attached is in the R configuration or the S configuration.

2. The method according to claim 1, wherein the compound has a single bond between carbon 22 and carbon 23.

3. The method according to claim 2, wherein carbon 24 is in the S configuration.

4. The method according to claim 1, wherein carbon 24 is in the R configuration.

5. The method according to claim 1, wherein the compound has a double bond in the E configuration between carbon 22 and carbon 23.

6. The method according to claim 5, wherein carbon 24 is in the S configuration.

7. The method according to claim 5, wherein carbon 24 is in the R configuration.

8. The method according to claim 1, wherein the subject is diagnosed with Crohn's disease.

9. The method according to claim 1, wherein the subject is a human subject.

10. The method according to claim 1, comprising administering 5 mcg to 500 mcg of the compound.

11. The method according to claim 1, comprising administering 1 to 4 doses per day of the composition.

12. The method according to claim 1, comprising administering 20 mcg to 1000 mcg of the compound in a delayed release composition.

13. The method according to claim 12, comprising administering the delayed release composition once per day.

14. The method according to claim 2, comprising administering the effective dose orally.

15. The method of claim 1, further comprising administering to the patient a compound selected from infliximab, adelimumab, certolizumab (CDP-870), interleukin-10, interleukin-4, 6-[(Aminocarbonyl)(2,6-difluorophenyl)amino]-2-(2,4-difluorophenyl)-3-pyridinecarboxamide (VX 702), 6-Chloro-5-[[(2R,5S)-4-[(4-fluorophenyl)methyl]-2,5-dimethyl-1-piperazinyl]carbonyl]-N,N,1-trimethyl-α-oxo-1H-Indole-3-acetamide (SCIO 469), doramapimod, ((2R)-2-((3R)-3-amino-3{4-[2-methyl-4-quinolinyl) methoxy] phenyl}-2-oxopyrrolidinyl)-N-hydroxy-4-methylpentanamide)) (DPC 333), pranalcasan, mycophenolate, merimepodib, cyclosporine, tacrolimus, pimecrolimus, 6-[(2S,3R,4R,6E)-3-hydroxy-4-methyl-2-(methylamino)-6,8-nonadienoic acid]-Cyclosporin A (ISAtx247), 5-aminosalicylic acid, mesalamine, sulfasalazine, balsalazide disodium, olsalazine sodium, methotrexate, azathioprine, SCIO 323 and alosetron.

16. The method of claim 1, comprising administering to the patient a composition comprising CARD-024 and a compound selected from infliximab, adelimumab, certolizumab (CDP-870), interleukin-10, interleukin-4,6-[(Aminocarbonyl)(2,6-difluorophenyl)amino]-2-(2,4-difluorophenyl)-3-pyridinecarboxamide (VX 702), 6-Chloro-5-[[(2R,5S)-4-[(4-fluorophenyl)methyl]-2,5-dimethyl-1-piperazinyl]carbonyl]-N,N,1-trimethyl-α-oxo-1H-Indole-3-acetamide (SCIO 469), doramapimod, ((2R)-2-((3R)-3-amino-3{4-[2-methyl-4-quinolinyl) methoxy] phenyl}-2-oxopyrrolidinyl)-N-hydroxy-4-methylpentanamide)) (DPC 333), pranalcasan, mycophenolate, merimepodib, cyclosporine, tacrolimus, pimecrolimus, 6-[(2S,3R,4R,6E)-3-hydroxy-4-methyl-2-(methylamino)-6,8-nonadienoic acid]-Cyclosporin A (ISAtx247), 5-aminosalicylic acid, mesalamine, sulfasalazine, balsalazide disodium, olsalazine sodium, methotrexate, azathioprine, SCIO 323, and alosetron.

17. The method of claim 8, comprising administering to the patient a compound selected from infliximab, adelimumab, certolizumab (CDP-870), interleukin-10, interleukin-4, 6-[(Aminocarbonyl)(2,6-difluorophenyl)amino]-2-(2,4-difluorophenyl)-3-pyridinecarboxamide (VX 702), 6-Chloro-5-[[(2R5S)-4-[(4-fluorophenyl)methyl]-2,5-dimethyl-1-piperazinyl]carbonyl]-N,N,1-trimethyl-α-oxo-1H-Indole-3-acetamide (SCIO 469), doramapimod, ((2R)-2-((3R)-3-amino-3{4-[2-methyl-4-quinolinyl) methoxy] phenyl}-2-oxopyrrolidinyl)-N-hydroxy-4-methylpentanamide)) (DPC 333), pranalcasan, mycophenolate, merimepodib, cyclosporine, tacrolimus, pimecrolimus, 6-[(2S,3R,4R,6E)-3-hydroxy-4-methyl-2-(methylamino)-6,8-nonadienoic acid]-Cyclosporin A (ISAtx247), 5-aminosalicylic acid, mesalamine, sulfasalazine, balsalazide disodium, olsalazine sodium, methotrexate, azathioprine, SCIO 323 and alosetron.

18. The method of claim 8, comprising administering to the patient a composition comprising CARD-024 and a compound selected from infliximab, adelimumab, certolizumab (CDP-870), interleukin-10, interleukin-4,6-[(Aminocarbonyl)(2,6-difluorophenyl)amino]-2-(2,4-difluorophenyl)-3-pyridinecarboxamide (VX 702), 6-Chloro-5-[[(2R,5S)-4-[(4-fluorophenyl)methyl]-2,5-dimethyl-1-piperazinyl]carbonyl]-N,N,1-trimethyl-α-oxo-1H-1-Indole-3-acetamide (SCIO 469), doramapimod, ((2R)-2-((3R)-3-amino-3{4-[2-methyl-4-quinolinyl) methoxy] phenyl}-2-oxopyrrolidinyl)-N-hydroxy-4-methylpentanamide)) (DPC 333), pranalcasan, mycophenolate, merimepodib, cyclosporine, tacrolimus, pimecrolimus, 6-[(2S,3R,4R,6E)-3-hydroxy-4-methyl-2-(methylamino)-6,8-nonadienoic acid]-Cyclosporin A (ISAtx247), 5-aminosalicylic acid, mesalamine, sulfasalazine, balsalazide disodium, olsalazine sodium, methotrexate, azathioprine, SCIO 323 and alosetron.

\* \* \* \* \*